United States Patent [19]

Matsushita et al.

[11] Patent Number: 4,871,858

[45] Date of Patent: Oct. 3, 1989

[54] METHOD OF PRODUCING FORMAMIDE COMPOUNDS

[75] Inventors: Hajime Matsushita, Yokohama; Makoto Shibagaki, Kawasaki; Kyoko Takahashi, Tokyo, all of Japan

[73] Assignee: Japan Tobacco Inc., Tokyo, Japan

[21] Appl. No.: 129,663

[22] Filed: Dec. 7, 1987

[30] Foreign Application Priority Data

Dec. 11, 1986 [JP] Japan ................................ 61-293468

[51] Int. Cl.$^4$ .................. C07D 401/04; C07D 211/22; C07C 103/22; C07C 103/37
[52] U.S. Cl. .................................... 546/244; 546/281; 564/215; 564/217; 564/218; 548/538
[58] Field of Search ................ 546/281, 244; 548/538; 564/215, 217, 218

[56] References Cited

U.S. PATENT DOCUMENTS 3,056,817 10/1962 Werber et al. ................... 260/404.8
3,558,619 1/1971 Hoffman et al. .................... 544/176

FOREIGN PATENT DOCUMENTS 1930827    1/1970  Fed. Rep. of Germany ...... 564/217
230527A3  12/1985  German Democratic Rep. .................................... 564/217

OTHER PUBLICATIONS

Chemical Abstracts, vol. 89, No. 7, Aug. 14, 1978, Columbus, Ohio, USA.
Synthesis, Jun. 1973, Stuttgart, New York, London.

Primary Examiner—Alan L. Rotman
Attorney, Agent, or Firm—Nixon & Vanderhye

[57] ABSTRACT

An amine is reached with dimethyformamioe in the presence of a solid catalyst to produce a formamide corresponding to the amine. The solid catalyst includes an oxide of metals belonging to Groups III, IV and V of the Periodic Table.

9 Claims, No Drawings

METHOD OF PRODUCING FORMAMIDE COMPOUNDS

BACKGROUND OF THE INVENTION

1. Field of the Invention

The present invention relates to a method of producing formamide compounds and, more particularly, to a method of producing formamide compounds by formylating amines via transamidation.

2. Description of the Prior Art

Formylated compounds of amines, i.e., formamides are very important materials as solvents, drugs, pesticides as well as intermediates for preparing such solvents, drugs, and pesticides in chemical industries. In order to derive nicotine from nornicotine, it is preferable to produce nicotine via N'-formylnornicotine as an intermediate rather than direct methylation of nornicotine.

Two methods are known for formylating amines. One method involves reaction of an amine with carbon monoxide under heating and high pressure. Another method involves reaction of an amine with separately prepared phenyl formate. However, these methods require relatively complicated reaction procedures and expensive apparatuses.

Another method is also known for producing formamide compounds by formylating amines via transamidation. This method consists of reacting dimethylformamide with an amine under the formylation conditions of the amine. This method has advantages in that dimethylformamide is commercially available at low cost, formylation can be easily performed, and a special apparatus is not needed. In the transamidation reaction, the following equilibrium reaction is established:

$$(CH_3)_2NCHO + R^1R^2NH \rightleftharpoons (CH_3)_2NH + R^1R^2NCHO$$

In this reaction, the reactants can be transferred to the products without using a catalyst, by heating to a high temperature to remove the dimethylamine. (Synthesis, 1973, P. 361). This formylation method can indeed produce a desired formamide compound with a high yield, but a long reaction time is required.

In the above literature, an acid catalyst such as sulfuric acid is used in the formylation reaction. When the acid catalyst is used, the reaction time can be shortened to some extent, but other problems such as corrosion of a reaction chamber occur. In addition, since the acid catalyst is a homogeneous catalyst, the reaction product must be washed to remove the acid catalyst after the reaction, and a problem of posttreatments, e.g., a waste fluid disposition, occurs.

As described above, in the conventional method of producing formamide compounds on the basis of the reaction of dimethylformamide and amines, the long reaction time is required if the catalyst is not used. If the acid catalyst is used, the reaction chamber is corroded, and post-treatments are required.

SUMMARY OF THE INVENTION

It is, therefore, an object of the present invention to provide a method of producing formamide on the basis of formylation of amines with dimethylformamide, wherein the reaction can be completed within a relatively short period of time and the post-treatment after the reaction can be easily performed.

According to the present invention, there is provided a method of producing a formamide compound which comprises reacting dimethylformamide and an amine in the presence of a solid catalyst comprising at least one metal oxide selected from the group consisting of oxides of metals of Groups III, IV, and V of the Periodic Table.

DETAILED DESCRIPTION OF THE PREFERRED EMBODIMENTS

According to the present invention, in formylation of an amine with dimethylformamide, a catalyst is used which comprises a metal oxide selected from the group consisting of oxides of metals of Groups III, IV, and V of the Periodic Table. Examples of the catalyst include silica gel, titania, zirconia, alumina, silica alumina, and natural or synthetic zeolite. These catalysts are commercially available at low cost and can be used in the form of granules or powders.

The present inventors have made studies on catalysts used in a reaction between dimethylformamide and an amine compound to find that the solid catalyst of the above-mentioned metal oxide can sufficiently accelerate the formylation reaction of the amine and can be easily separated and recovered after reaction because this catalyst is a heterogeneous catalyst.

Since the reaction to which the above-mentioned solid catalyst is applied is a known reaction between dimethylformamide and the amine, an amine used as a material for the formylation reaction may be a primary amine or a secondary amine (excluding dimethylamine) including an aliphatic amine, an alicyclic amine, an aromatic amine, and a heterocyclic amine. Examples of such an amine are an alkylamine (e.g., ethylamine, propylamine, isopropylamine, butylamine, decylamine, benzylamine, or α-methylbenzylamine), dialkylamine, a cycloalkylamine (e.g., cycloalkylamine having 3 to 8 carbon atoms), dicycloalkylamine, an aromatic amine (e.g., phenylamine or naphthylamine), and a heterocyclic amine (e.g., piperidine, pyrrolidine, or nornicotine).

The formylation reaction of the amine with dimethylformamide can be performed by bringing the amine into contact with dimethylformamide in the presence of the catalyst of the present invention under the formylation conditions for the amine. This reaction can be performed in the gaseous or liquid phase. In addition, the reaction is relatively simple and safe and can be performed regardless of the scale of reaction system.

In order to perform the formylation reaction in the liquid phase, the above-mentioned catalyst is added to a dimethylformamide solution (i.e., an excessive amount of dimethylformamide is present) containing the amine, and the resultant solution is heated. The catalyst can be used in an amount of 0.01 to 10 g, preferably 0.5 to 3 g, per millimole of the amine. The reaction is generally carried out at a temperature of 100° C. to 180° C. and is usually performed under reflux. In this reaction, an appropriate inert diluting solvent may be added to dilute the reaction mixture. After the reaction, the catalyst is removed by filtering, and the filtered reaction mixture is subjected to fractional distillation to isolate the formamide compound formed. In this case, if the produced formamide compound has a boiling point sufficiently higher than that of dimethylformamide, dimethylformamide is simply evaporated to obtain a formamide compound having a sufficiently high purity. The catalyst recovered by filtration can be repeatedly used in the formylation reaction.

In order to perform the formylation reaction in the gaseous phase, the catalyst is filled in a reaction tube and is heated to a predetermined reaction temperature. The dimethylformamide solution of the amine is supplied to the filled catalyst layer directly or by using a proper inert carrier gas. The outlet of the reaction tube is cooled by a coolant such as water or ice to condense the produced formamide compound and the nonreacted material. The produced formamide compound can be separated from the condensate following the same procedures as in the liquid-phase reaction described above.

The present invention will be described in detail by way of its examples.

EXAMPLE 1

0.5 g of a silica gel powder catalyst (100 mesh, available from Marinecrot Corp.), 2 millimole of piperidine and 20 millimole of dimethylformamide were charged in a 50-ml round bottom flask, and the resultant mixture was heated and refluxed moderately. Small portions of the reacted solution were sampled after 2 and 5 hours of refluxing to measure yields of the desired product, N-formylpiperidine, by using a gas chromatograph. The yields were 67% and 100% after 2 and 5 hours, respectively.

The same procedures as described above were performed except that active alumina C-1A (tradename) available from Mizusawa Kagaku Kogyo K.K., titania (anatase) available from Wako Junyaku Kogyo KK, silica alumina (the grain size: 24 to 60 meshes after pulverization) available from Mizusawa Kagaku Kogyo K.K., zirconia (grain size: 24 to 60 meshes after pulverization of pellets) available from Daiichi Kigenso Kagaku Kogyo K.K., and zeolite A-3 (tradename) (grain size: 24 to 60 meshes after pulverization of balls) available from Toyo Soda Kogyo K.K. were used in place of silica gel. Results are shown in Table 1 below, which includes the results of using silica gel.

TABLE 1

| Catalyst | Yield of N—Formylpiperidine | |
|---|---|---|
| | After 2 hours (%) | After 5 hours (%) |
| Silica Gel | 67 | 100 |
| Alumina | 56 | 100 |
| Titania | 52 | 100 |
| Silica Alumina | 61 | 100 |
| Zirconia | 1 | 3 |
| Zeolite | 11 | 28 |

When zirconia and zeolite were used, the yields were lower than those for other catalysts. However, it is seen that these catalysts accelerate the N-formylpiperidine-producing reaction by formylation after short period of time, which was difficult in the conventional methods.

EXAMPLE 2

2 g of zirconia particles as in Example 1 were filled in a glass tube having an inner diameter of 6.5 mm and an outer diameter of 8.5 mm. The glass tube was placed in an electric furnace. This reaction system was heated to 250° C., and a solution of 10 millimole of cyclohexylamine in 50 ml of dimethylformamide was supplied at a rate of 5 ml/min by a microfeeder while nitrogen gas was supplied at a rate of 60 ml/min to the glass tube. The material passing through the catalyst layer filled in the glass tube was cooled and condensed at the outlet of the glass tube.

The resultant reaction mixture was subjected to quantitative measurement of the desired product, N-formylcyclohexylamine, by using a gas chromatograph. The yield was 85%, and the remaining component was cyclohexylamine.

EXAMPLE 3

0.5 g of silica gel as in Example 1, 2 millimole of α-methylbenzylamine and 20 millimole of dimethylformamide were charged in a 50-ml round bottom flask. The resultant reaction mixture was heated and refluxed. A portion of the reaction mixture was sampled after two hours of refluxing and was analyzed using a gas chromatograph. α-methylbenzylamine as a starting material was not detected, and N-formyl-α-methylbenzylamine was found to be produced at a yield of 89%.

The same procedures as described above were followed, except that dicyclohexylamine, cyclohexylamine, decylamine, or pyrrolidine was used in place of α-methylbenzylamine. Results are shown in Table 2 below, in which results of using α-methylbenzylamine are also listed.

TABLE 2

| Amine | Product | Reaction Time (hours) | Yield (%) |
|---|---|---|---|
| α-methylbenzyl-amine | N—formyl-α-methylbenzyl-amine | 2 | 89 |
| Dicyclohexyl-amine | N—formyldicyclo-hexylamine | 5 | 66 |
| Cyclohexyl-amine | N—formylcyclo-hexylamine | 3 | 93 |
| Decylamine | N—formyldecylamine | 5 | 84 |
| Pyrrolidine | N—formylpyrrolidine | 3 | 100 |

EXAMPLE 4

1.48 g of racemic-nornicotine were dissolved in 30 ml of dimethylformamide, and 1 g of titania as in Example 1 was added. The resultant mixture was heated and refluxed moderately for 5 hours. The mixture was then cooled to room temperature and the titania was removed from the reaction mixture by filtering. The filtrate was concentrated by removing dimethylformamide under reduced pressure. The desired product, N'-formylnornicotine, was gradually precipitated during concentration. By completely removing dimethylformamide, 1.55 g (yield: 88.1%) of N'-formylnornicotine were obtained.

According to the present invention as described above, the formamide compound can be produced within a relatively short period of reaction time. In addition, the catalyst can be easily recovered after the reaction, and the separation of the product can also be easily performed.

What is claimed is:

1. A method of producing a formamide compound in liquid phase comprising the steps of:
   (a) preparing a mixture containing (1) a solution of an amine reactant in dimethylformamide, and (2) a solid catalyst comprising a metal oxide selected from the group consisting of silica gel, titania, zirconia, alumina, silica alumina, and zeolite, said amine reactant being a member selected from the group consisting of an "alkyl amine having 2-10 carbon atoms, cycloalkylamine having 3 to 8 carbon atoms, dicyclohexylamine, phenylamine, naphthylamine, benzylamine, α-benzylamine, pyrrolidine, piperidine or nornicotine";

(b) placing said mixture under formylation conditions for said amine reactant with said dimethylformamide to produce a formamide compound corresponding to said amine, said formylation conditions including heating said mixture at a temperature of 100° C. to 180° C.;

(c) removing said solid catalyst from said mixture; and (d) separating the thus-produced formamide compound from the mixture.

2. The method according to claim 1 wherein said mixture is heated under refluxing.

3. A method of producing of formamide compound in gaseous phase, comprising the steps of:

(a) heating a mixture of an amine reactant and dimethylformamide to a temperature sufficient to vaporize said mixture, said amine reactant being a member selected from the group consisting of an "alkyl amine having 2–10 carbon atoms, cycloalkylamine having 3 to 8 carbon atoms, dicyclohexylamine, phenylamine, naphthylamine, benzylamine, α-benzylamine, pyrrolidine, piperidine or nornicotine";

(b) bringing said vaporized mixture into contact with a solid catalyst bed comprising a metal oxide selected from the group consisting of silica gel, titania, zirconia, alumina, silica alumina and zeolite to react said amine reactant with said dimethylformamide, thereby producing the corresponding formamide compound;

(c) cooling and condensing the gaseous mixture containing the produced formamide compound; and (d) separating the thus-produced formamide compound from the condensate.

4. The method according to claim 1 or 3, wherein said amine reactant has 2 to 10 carbon atoms.

5. The method according to claim 1 or 3, wherein said amine is a primary or secondary amine.

6. The method according to claim 1 or 3, wherein said amine is ethylamine, propylamine, isopropylamine, butylamine, decylamine, benzylamine, α-methylbenzylamine, cyclohexylamine, dicyclohexylamine, phenylamine, naphthylamine, piperidine, pyrrolidine, or nornicotine.

7. The method according to claim 1, wherein said solid catalyst is used in an amount of 0.01 to 10 g per millimole of said amine.

8. The method according to claim 1, wherein said solid catalyst is used in an amount of 0.5 to 3 g per millimole of said amine.

9. The method according to claim 3, wherein said vaporized mixture is carried by an inert carrier gas.

* * * * *